(12) United States Patent
Chono et al.

(10) Patent No.: US 8,852,915 B2
(45) Date of Patent: Oct. 7, 2014

(54) METHOD OF RETROVIRUS STORAGE

(71) Applicant: Takara Bio Inc., Shiga (JP)

(72) Inventors: Hideto Chono, Shiga (JP); Yasushi Katayama, Shiga (JP); Hiromi Okuyama, Shiga (JP); Junichi Mineno, Shiga (JP); Kiyozo Asada, Shiga (JP); Ikunoshin Kato, Shiga (JP)

(73) Assignee: Takara Bio Inc., Shiga (JP)

( * ) Notice: Subject to any disclaimer, the term of this patent is extended or adjusted under 35 U.S.C. 154(b) by 0 days.

(21) Appl. No.: 13/650,594

(22) Filed: Oct. 12, 2012

(65) Prior Publication Data

US 2013/0102048 A1    Apr. 25, 2013

Related U.S. Application Data

(63) Continuation of application No. 11/815,681, filed as application No. PCT/JP2006/301971 on Feb. 6, 2006, now abandoned.

(30) Foreign Application Priority Data

Feb. 7, 2005    (JP) ................................ 2005-031000

(51) Int. Cl.
*C12N 11/02* (2006.01)
*C12N 7/00* (2006.01)

(52) U.S. Cl.
CPC ...... *C12N 11/02* (2013.01); *C12N 2740/10051* (2013.01); *C12N 7/00* (2013.01)
USPC ........................................ 435/239; 435/235.1

(58) Field of Classification Search
CPC ..................... C12N 7/00; C12N 15/86; C12N 2740/10022; C12N 2740/13043; C12N 2740/13045; C12N 2810/10; C12N 2810/80; C12N 2810/851; C12N 2810/859; C12N 11/02; C12N 2740/10051; C12N 2740/15021; C12N 2740/15022; C12N 2740/15051
See application file for complete search history.

(56) References Cited

U.S. PATENT DOCUMENTS

| 5,686,278 A | 11/1997 | Williams et al. |
| 6,426,042 B1 | 7/2002 | Asada et al. |
| 2001/0055586 A1 | 12/2001 | Valerio et al. |
| 2004/0058447 A1 | 3/2004 | Ueno et al. |
| 2006/0063260 A1 | 3/2006 | Volkmer et al. |

FOREIGN PATENT DOCUMENTS

| CN | 1207774 A | 2/1999 |
| CN | 1314947 A | 9/2001 |
| EP | 0870839 A1 | 10/1998 |
| WO | 00/01836 A1 | 1/2000 |
| WO | 03/093462 A2 | 11/2003 |
| WO | 2004/036992 A2 | 5/2004 |
| WO | 2004078906 A2 | 9/2004 |

OTHER PUBLICATIONS

Office Action issued in corresponding Japanese Patent Application No. 2007-501659, mailed Apr. 3, 2012, and English translation thereof.
First Office Action of State Intellectual Property Office, P.R. China, Patent Appln. No. 200680004201.2; issued Jun. 26, 2009.
English translation of the Office Action in the corresponding Chinese Patent Application No. 2006-80004201.2 issued on Oct. 20, 2010.
Office Action issued in corresponding Korean Patent Application No. 2007-7020107, mailed Dec. 27. 2010, and English translation thereof (as embedded in the partial reporting letter).
Office Action issued in corresponding Japanese Patent Application No. 2007-501659, mailed Jun. 7, 2011, and English translation thereof.
Office Action issued in corresponding Chinese Patent Application No. 200680004201.2, mailed Jul. 6, 2011, and English translation thereof.
Office Action issued in corresponding Korean Patent Application No. 10-2011-7025412, mailed Dec. 16, 2011, and English translation thereof.
Office Action issued in corresponding Japanese Patent Application No. 2012-130073, mailed Jan. 14, 2014, and English translation thereof.

*Primary Examiner* — Blaine Lankford
(74) *Attorney, Agent, or Firm* — Browdy and Neimark, PLLC

(57) ABSTRACT

A method of retrovirus storage, characterized in that a retrovirus is sustained in the presence of a substance with retrovirus binding activity immobilized on a solid phase. Further, there is provided a retrovirus composition characterized in that a retrovirus in the form of binding to a substance with retrovirus binding activity is sealed in a container holding a solid phase having the substance with retrovirus binding activity immobilized thereon.

9 Claims, 1 Drawing Sheet

METHOD OF RETROVIRUS STORAGE

TECHNICAL FIELD

The present invention relates to a method for purifying or storing a retrovirus vector used for transforming a cell by gene transfer in the fields of medicine, pharmacy, agriculture, forestry and fisheries as well as food science, and a series of techniques related thereto.

BACKGROUND ART

Retrovirus vectors can be used to surely integrate genes of interest into host chromosomes. For this reason, these vectors are widely used in the field of gene therapy centering on ex vivo gene therapy protocols that target hematopoietic stem cells or peripheral blood lymphocytes. They also are widely used in the field of basic research as tools for gene expression analyses. This is because they can be used to achieve stable expression levels of foreign (inserted) genes. Usually, a culture supernatant of a producer cell is filtrated through a filter and the filtrate is used as a retrovirus vector. The filtrate may be subjected to further purification if the retrovirus vector is to be used for an ex vivo gene therapy protocol. However, there have been problems concerning the above because the purification of a virus vector is complicated and the recovery is low. No scientific literature describing the stability of a purified virus vector is found.

A culture supernatant of a retrovirus vector producer cell is usually stored after filtration through a filter in a frozen state in a deep freezer. The stability of a thawed vector in a solution state is low. The half-life has been reported to be 92 hours at 4° C., 18-64 hours at 0° C., 11-39 hours at 32° C., or 7-9 hours at 37° C. (Non-patent Document 1, Non-patent Document 2). Since the stability of a retrovirus vector is low as described above, a cryopreserved retrovirus vector is usually thawed upon use and used immediately.

A method in which a recombinant retrovirus is lyophilized and then stored is described in Patent Document 1. This method requires equipment for lyophilization, and a procedure for reconstituting the stored recombinant retrovirus upon use.

A gene transfer method in which a retrovirus is subjected to infection in the presence of a substance having a retrovirus-binding activity (in particular, a fibronectin fragment) is described in Patent Document 2, Patent Document 3 or Non-patent Document 3. The influence of such a substance on the stability of a retrovirus is unknown.

Patent Document 1: U.S. Pat. No. 5,792,643
Patent Document 2: WO 95/26200
Patent Document 3: WO 97/18318
Non-patent Document 1: McTaggart, S., Al-Rubeai, M., Biotechnol. Prog., 16(5):859-865 (2000)
Non-patent Document 2: Kaptein, L. C., et al., Gene Ther., 4(2):172-176 (1997)
Non-patent Document 3: Hanenberg, H. et al., Nat. Med., 2(8):876-882 (1996)

DISCLOSURE OF INVENTION

Problems to be Solved by the Invention

As described above, one must rapidly handle a cryopreserved retrovirus vector after thawing it and use to infect a cell in a short time. Thus, if the schedule of infection step is upset for some reason (e.g., delayed growth of a cell to be infected with a retrovirus vector) and a retrovirus vector cannot be used to infect a cell immediately after thawing, sufficient infection efficiency may not be achieved.

Thus, a method by which a retrovirus vector can be stably stored in a state ready for immediate use has been desired.

Means to Solve the Problems

The present inventors attempted to develop a method for stably storing a retrovirus at a low temperature without freezing while retaining the gene transfer activity. As a result of intensive studies, the present inventors have found that a retrovirus can be stably stored in a state ready for immediate use even in an unfrozen state by maintaining the retrovirus at a low temperature being bound to a solid support coated with a substance having a virus-binding activity. Thus, the present invention has been completed.

The first aspect of the present invention relates to a method for storing a retrovirus, the method comprising maintaining a retrovirus in the presence of a substance having a retrovirus-binding activity immobilized on a solid support.

According to the first aspect, the retrovirus can be maintained in an unfrozen state. For example, the retrovirus may be maintained in a solution so that the solution is not in contact with air in one embodiment of the storage method.

According to the first aspect, the retrovirus may be separated from other retrovirus producer cell-derived components. For example, the retrovirus can be maintained in a buffer containing a phosphate salt as a buffering component in this embodiment. In addition, the retrovirus may be maintained using as the buffer a solution containing a substance selected from the group consisting of proteins and saccharides.

Examples of the substances having a retrovirus-binding activity used according to the method for storing a retrovirus of the first aspect include a polypeptide having the heparin-II domain of fibronectin, fibroblast growth factor, a polypeptide having the insulin-binding domain of type V collagen, DEAE-dextran and polylysine.

The second aspect of the present invention relates to a composition containing a retrovirus, wherein the composition is contained in a container carrying a solid support on which a substance having a retrovirus-binding activity is immobilized, and the retrovirus is bound to the substance having a retrovirus-binding activity.

For example, the retrovirus in the composition of the second aspect may be contained in a solution in the container so that the solution is not in contact with air.

In the composition of the second aspect, the retrovirus may be contained being separated from other retrovirus producer cell-derived components. The composition can contain a buffer containing a phosphate salt as a buffering component. In addition, the composition may contain a substance selected from the group consisting of proteins and saccharides in a solution.

Examples of the substances having a retrovirus-binding activity used for storing a retrovirus according to the second aspect include a polypeptide having the heparin-II domain of fibronectin, fibroblast growth factor, a polypeptide having the insulin-binding domain of type V collagen, DEAE-dextran and polylysine.

Effects of the Invention

According to the present invention, a retrovirus can be stored so that it can be immediately subjected to gene transfer. It is possible to conduct gene transfer with reproducibility because retrovirus-bound containers of the same quality can be stably stored. Furthermore, the present invention enables transportation at a low temperature if a gas-permeable cell culture bag or separation bag is used as a storage container to keep a closed system.

BEST MODE FOR CARRYING OUT THE INVENTION

Figure 1:
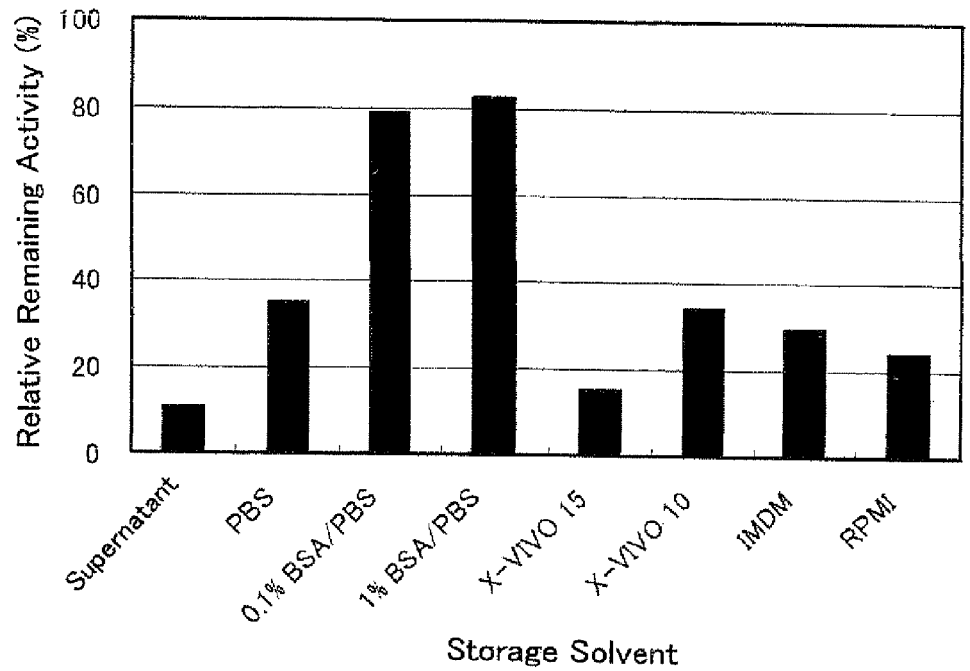
FIG. 1 shows values of gene transfer efficiency relative to transfer efficiency observed for the control.

There is no specific limitation concerning the retrovirus used according to the present invention. For gene transfer, an artificially modified recombinant retrovirus (i.e., a retrovirus vector) is usually used according to the present invention. Particularly, a replication-defective retrovirus vector is preferable for preventing unlimited infection or gene transfer. Such a vector is made replication-defective so that it cannot autonomously replicate in an infected cell and therefore avirulent. Such a vector can invade a host cell such as a vertebrate cell (particularly a mammalian cell) to stably integrate a foreign gene, which is inserted in the vector, into the chromosomal DNA. Examples of known replication-defective retrovirus vectors include retrovirus vectors (e.g., MFG vector, α-SGC vector (WO 92/07943), pBabe (Morgenstern, J. P., Land, H., Nucleic Acids Research, 18(12):3587-3596 (1990)), pLXIN (Clontech) or pDON-AI (Takara Bio)), lentivirus vectors (human immunodeficiency virus (HIV)-derived vectors, simian immunodeficiency virus (SIV)-derived vectors, etc.) and modifications thereof.

There is no specific limitation concerning the foreign gene carried by the retrovirus vector. Any gene of which the expression in the cell of interest is desired can be inserted. Examples thereof include genes encoding polypeptides (enzymes, growth factors, cytokines, receptors, structural proteins, etc.), antisense RNAs, ribozymes, decoys, and RNAs that cause RNA interference. It is possible according to the present invention to use the foreign gene being inserted into a retrovirus vector under the control of an appropriate promoter (e.g., an LTR promoter in the retrovirus vector or a foreign promoter). Another regulatory element which cooperates with the promoter and a transcription initiation site (e.g., an enhancer sequence) may be present in the vector in order to accomplish transcription of the foreign gene. Preferably, the transferred gene may contain a terminator sequence placed downstream. Furthermore, one may include an appropriate marker gene which enables selection of a cell having a transferred gene (e.g., a drug resistance gene, a gene encoding a fluorescent protein, a gene encoding an enzyme that can function as a reporter such as β-galactosidase or luciferase).

The retrovirus may be prepared according to a known method and used according to the present invention. There is no specific limitation concerning the preparation method. If a retrovirus vector is to be used, a culture supernatant collected from a culture of a retrovirus producer cell suitable for the retrovirus can be used according to the present invention. The retrovirus producer cell may be one that stably produces retrovirus particles in the supernatant or one that transiently produces retrovirus particles upon transfection with a retrovirus vector plasmid.

A known packaging cell line such as PG13 (ATCC CRL-10686), PA317 (ATCC CRL-9078), GP+E-86 or GP+envAm-12 (U.S. Pat. No. 5,278,056), or Psi-Crip (Danos, O., Mulligan, R. C., Proc. Natl. Acad. Sci. USA, 85(17):6460-6464 (1988)) may be used for preparing a retrovirus producer cell. 293 cell or 293T cell of which the transfection efficiency is high may be used for preparing a retrovirus producer cell.

According to the present invention, it is also possible to use a retrovirus prepared by pseudotyped packaging which has an envelope derived from a virus different from the one from which the genome of the retrovirus vector is derived. For example, a pseudotyped retrovirus having an envelope derived from Moloney murine leukemia virus (MoMLV), gibbon ape leukemia virus (GaLV), vesicular stomatitis virus (VSV) or feline endogenous virus, or a protein that can function as an envelope can be used. Furthermore, one may prepare a retrovirus vector having on its surface a protein that is subjected to sugar chain modification. The retrovirus vector may be prepared using a retrovirus producer cell having a transferred gene for an enzyme involved in glycosylation or the like. Such a retrovirus vector can also be used according to the present invention.

(A) The Method for Storing a Retrovirus of the Present Invention

The present invention provides a method for storing a retrovirus, the method comprising maintaining a retrovirus in the presence of a substance having a retrovirus-binding activity immobilized on a solid support in an unfrozen state.

There is no specific limitation concerning the container for storing a retrovirus used according to the method of the present invention as long as it is suitable for storage of a biological material (e.g., a cell or a body fluid sample) or can be used to culture cells. Examples thereof include culture plates, culture flasks, separation bags and gas-permeable culture bags.

According to the present invention, there is no specific limitation concerning the solid support on which a substance having a retrovirus-binding activity is to be immobilized. Solid supports in various forms including beads and fibers can be used. It is preferable for the present invention to use a solid support made of a material that does not have a harmful influence on maintenance or growth of cells when it is brought into contact with the cells during cell cultivation. In one preferred embodiment, the above-mentioned container for storing a retrovirus is used as a solid support for immobilizing a substance having a retrovirus-binding activity. In this embodiment, the surface of the container to be brought into contact with the content is coated with a substance having a retrovirus-binding activity. Examples of substances having a retrovirus-binding activity include fibronectin, a fibronectin fragment having the heparin-II domain (CH-296 (RetroNectin), CH-271, H-296, etc.), fibroblast growth factor, a polypeptide having the insulin-binding domain of type V collagen, DEAE-dextran and polylysine. There is no specific limitation concerning the method for immobilizing a substance having a retrovirus-binding activity on the surface of a solid support. A method suitable for the substance having a retrovirus-binding activity to be used may be selected. In an exemplary method, a buffer containing the substance is allowed to stand for a given period of time being in contact with a solid support to be used. Procedures for immobilizing the substance are also described in Patent Documents 2 and 3.

Although it is not intended to limit the present invention, it is preferable according to the present invention to reduce the amount of air that is in contact with a retrovirus-containing solution. A method in which a container to be used has a structure with which the solution can be held so that the solution is not in contact with air exemplifies one embodiment of the present invention. If a container of a fixed volume is to be used, this embodiment can be accomplished by filling the container with the retrovirus-containing solution. Alternatively, a solution of an arbitrary volume can be held so that the solution is not in contact with air. This is accomplished by using a container in a form of sack or bag composed of a film-like substrate of which the internal volume can be altered according to the volume of the solution. The container used according to the present invention preferably can hold a retrovirus-containing solution in a sealed or airtight state. More preferably, a commercially available cell culture bag can be used according to the present invention.

A supernatant collected using a retrovirus producer cell, a retrovirus purified from the supernatant or the like can be used as a retrovirus stored according to the present invention. For example, a supernatant or a purified retrovirus which was cryopreserved before may be stored in an unfrozen state according to the method of the present invention.

In one embodiment of the present invention, a retrovirus is stored being separated from other retrovirus producer cell-derived components. This embodiment is usually carried out with the following steps:

(1) a step of contacting a solid support on which a substance having a retrovirus-binding activity is immobilized with a retrovirus producer cell culture supernatant which contains the retrovirus;
(2) a step of washing the solid support of step (1); and
(3) a step of maintaining the solid support obtained in step (2) being in contact with a buffer.

If a retrovirus that has been purified beforehand is to be used in place of a supernatant of a retrovirus producer cell, step (2) may be omitted.

In this embodiment, the infectivity of a retrovirus is retained at a higher level because inactivation of the retrovirus due to a component contained in the supernatant of the retrovirus producer cell is suppressed.

There is no specific limitation concerning the method for binding a retrovirus to a substance having a retrovirus-binding activity. For example, the binding may be carried out as follows: a culture supernatant of a retrovirus producer cell is allowed to stand being in contact with a solid support on which the substance is immobilized; a retrovirus is precipitated on the surface of a solid support using centrifugal force; or a container containing a solid support and a retrovirus is shaken.

A supernatant is removed from a container to which a retrovirus is bound via a retrovirus-binding substance as a result of the above-mentioned procedure, the solid support (e.g., the container itself) is optionally washed, and a solution suitable for storage of the retrovirus is then added to the container.

There is no specific limitation concerning the solution used for washing a solid support to which a retrovirus is bound as long as it does not considerably reduce the infectivity of the retrovirus to be stored. For example, physiological saline, phosphate-buffered saline or the same medium as that used for culturing the retrovirus producer cell can be used. In particular, a solution used for storing a retrovirus as described below is preferably used. Since a supernatant of a retrovirus producer cell contains a substance that inhibits infection of a cell with a retrovirus, a retrovirus stored being separated from other retrovirus producer cell-derived components is advantageously used to infect a cell.

According to the present invention, a retrovirus is stored being bound to a retrovirus-binding substance and in contact with an appropriate solution. Although there is no specific limitation concerning the solution to be used in this step as long as it does not considerably reduce the infectivity of the retrovirus to be stored, a buffer containing a phosphate salt (sodium phosphate, potassium phosphate, etc.) as a buffering component is preferably used. The solution may further contain a saccharide (glucose, galactose, lactose, mannitol, etc.), a protein (albumin, collagen (gelatin), etc.) or another component (an inorganic salt, a polyol, human serum, etc.) as a component for stabilizing a retrovirus.

A retrovirus is stored in an unfrozen state according to the above-mentioned storage method. Nevertheless, the ability of the stored retrovirus to infect a cell is retained at a higher level than that observed for a retrovirus culture supernatant stored as it is. Although it is not intended to limit the present invention, a retrovirus is stored according to the present invention at a low temperature for a period of 24 hours or more, preferably 48 hours or more, more preferably 72 hours or more. As used herein, a low temperature refers to a temperature of 15° C. or below at which a solution to be stored does not freeze. Preferably, a retrovirus is stored at 0-10° C.

A retrovirus stored in a container according to the method of the present invention can be used for infection as it is. If the retrovirus is a recombinant retrovirus carrying a foreign gene, it is possible to transfer the gene into a cell by this procedure. For example, infection with a retrovirus can be carried out by adding to a container a cell of which the infection is desired after exchanging the solution in the container for a solution suitable for infection of the cell with the retrovirus (or without the exchange if the solution for storage is suitable for infection with the retrovirus). Alternatively, infection with a retrovirus can be carried out by adding a cell suspension to a storage container from which the contained solution has been removed. The infection step may be carried out in static culture. Alternatively, the infection step may be carried out according to a method in which a retrovirus is brought into contact with a cell by applying centrifugal force to precipitate the cell on the surface of a solid support on which a substance having a retrovirus-binding activity is immobilized. The target cell infected with the retrovirus may be cultured in the container as it is, or it may be transferred to another container after the above-mentioned procedure and then cultured.

If the retrovirus-binding substance also has an affinity for a target cell, the target cell and the retrovirus are co-localized on the surface of the container as a result of the above-mentioned procedure. Then, infection of the target cell with the retrovirus takes place with high efficiency. For example, gene transfer into a hematopoietic stem cell can be conveniently carried out with high efficiency by using a recombinant retrovirus carrying a foreign gene of interest and the polypeptide CH-296, which has a hematopoietic stem cell-binding activity.

A retrovirus storage method in which a solid support on which both a substance having a retrovirus-binding activity and a substance having a target cell-binding activity are immobilized is used exemplifies another embodiment of the present invention. According to this method, a container in which a retrovirus is stored together with a substance having a retrovirus-binding activity and a substance having a target cell-binding activity can be used as a container for infection of a target cell with a retrovirus. Thus, the method is particularly useful in the field of gene therapy for which highly efficient and/or cell-selective gene transfer is desired.

Examples of substances having a target cell-binding activity used in the above-mentioned embodiment include, but are not limited to, a protein or peptide that is capable of recognizing a target cell (an antibody or a receptor that recognizes a component on the surface of a target cell, a ligand for a receptor on the surface of a target cell (a growth factor, a hormone, a cytokine, etc.)), a lectin, a sugar chain and a glycolipid. Such substances and methods for immobilizing the same are also described in Non-patent Document 3.

(B) The Composition of the Present Invention

The present invention provides a retrovirus-containing composition which is in a form suitable for storage.

A retrovirus in the composition is contained in a container being bound to a substance having a retrovirus-binding activity immobilized on a solid support. The composition can be prepared in accordance with the above description regarding the retrovirus storage method. The substance having a retrovirus-binding activity is exemplified by the above-mentioned one that can be used according to the retrovirus storage method.

In one embodiment of the present invention, an exemplary composition contains a retrovirus in a solution so that the solution is not in contact with air. The composition may be separated from other retrovirus producer cell-derived components. In this case, the composition preferably further contains a solution suitable for storage of a retrovirus. The above-mentioned solution that can be used according to the retrovirus storage method may be used as the solution suitable for storage of a retrovirus.

Although there is no specific limitation concerning the container used according to the present invention as long as it is suitable for storage of a biological material (e.g., a cell or a body fluid sample) or can be used to culture cells, the container preferably can hold a retrovirus-containing solution in a sealed or airtight state. For example, a commercially available cell culture bag can be used.

The retrovirus-containing composition of the present invention has excellent storage stability and can be immediately used to infect a cell with a retrovirus. Thus, it is useful for studies of retroviruses and in the field of medicine, particularly in the field of gene therapy in which recombinant retrovirus vectors are used.

Examples

The following Examples illustrate the present invention in more detail, but are not to be construed to limit the scope thereof.

Example 1

1. Preparation of CH-296-Coated Plate

500 µl of a fibronectin fragment CH-296 (product name: RetroNectin; Takara Bio) at a concentration of 20 µg/ml was added to each well of a 24-well plate without surface treatment (Falcon). The plate was allowed to stand at 4° C. overnight, subjected to blocking with 2% BSA/PBS at room temperature for 30 minutes, and washed with PBS. This plate was used as a CH-296-coated plate and prepared when necessary.

2. Preparation of Retrovirus Vector

A retrovirus vector plasmid pDOG-polII was constructed as follows. First, an rsGFP expression vector pQBI25 (Qbiogene) was cleaved with restriction enzymes NheI and NotI to obtain a 775-bp GFP gene fragment. Next, pQBI polII (Qbiogene) was cleaved with restriction enzymes NheI and NotI to remove an rsGFP-NeoR fusion gene. The previously obtained 775-bp rsGFP gene fragment was inserted to obtain a vector pQBI polII(neo-) in which the rsGFP gene is expressed under the control of polII promoter. pQBI polII(neo-) was digested with a restriction enzyme XhoI to obtain a DNA fragment containing a GFP expression unit under the control of polII promoter. The termini were blunted using DNA Blunting Kit (Takara Bio). Termini of a 4.58-kbp vector fragment obtained by digesting a retrovirus vector plasmid pDON-AI (Takara Bio) with restriction enzymes XhoI and SphI were blunted using DNA Blunting Kit (Takara Bio), and then dephosphorylated using alkaline phosphatase (Takara Bio). The previously blunted DNA fragment containing the rsGFP expression unit under the control of polII promoter was inserted into this blunted vector using DNA Ligation Kit (Takara Bio) to obtain an rsGFP expression recombinant retrovirus vector pDOG-polII.

Transient virus production was carried out using the vector pDOG-polII and Retrovirus Packaging Kit Eco (Takara Bio) to obtain an ecotropic virus DOG-polII. The ecotropic virus DOG-polII was used to infect a GaLV retrovirus packaging cell PG13 (ATCC CRL-10686) in the presence of RetroNectin (Takara Bio) to obtain a gene-transferred cell PG13/DOG-polII. PG13/DOG-polII was cultured in Dulbecco's modified Eagle medium (DMEM, Sigma) containing 10% fetal calf serum (Thermo Trace). When the cell was grown to semi-confluence, the medium was exchanged for 0.1 ml/cm² of fresh DMEM containing 10% fetal calf serum. After 24 hours, the supernatant was filtrated through a 0.45-µm filter (Millipore) to obtain a GaLV/DOG-polII virus supernatant. Aliquots of the thus obtained virus supernatant were stored in a freezer at −80° C. and subjected to subsequent storage and gene transfer experiments.

3. Measurement of Titer of Virus Supernatant

A titer of a virus supernatant was measured using HT-1080 cells (ATCC CCL-121) according to a standard method (Markowitz, D. et al., J. Virol., 62(4):1120-1124 (1988)). Specifically, $5 \times 10^4$ HT-1080 cells in 2 ml of DMEM containing 10% fetal calf serum were added to each well of a 6-well tissue culture plate, and cultured overnight at 37° C. with 5% $CO_2$. The medium was removed by suction, 1 ml of a serial dilution of the virus supernatant was added to the well, and hexadimethrine bromide (polybrene, Aldrich) at a final concentration of 8 µg/ml was further added thereto. The cells were cultured at 37° C. with 5% $CO_2$ for 4 to 6 hours. 1 ml of DMEM containing 10% fetal calf serum was further added thereto, and the cultivation was continues for 72 hours. The cells collected from the plate were subjected to analysis using a flow cytometer FACS Vantage (Becton-Dickinson), and the ratio of HT-1080 cells expressing rsGFP was determined. The number of infectious particles in 1 ml of a supernatant (I.V.P./ml) was calculated based on a value obtained by multiplying the number of input cells per well by the ratio of rsGFP-expressing cells and the dilution rate of the virus supernatant to determine the virus titer. The titers of virus supernatant prepared in Example 1-2 ranged from $1.9 \times 10^5$ I.V.P./ml to $4.5 \times 10^5$ I.V.P./ml.

Example 2

Storage of Retrovirus Using CH-296-Coated Plate (1)

K-562 cells (ATCC CCL-243) were used for assessment of the activity of the GaLV/DOG-polII virus supernatant. K-562 cells were cultured in RPMI-1640 medium (Sigma) containing 10% fetal calf serum (Thermo Trace).

250 µl of the GaLV/DOG-polII virus supernatant (the original concentration) was added to each well of a 24-well CH-296-coated plate, and the plate was incubated in 5% $CO_2$ incubator at 37° C. for 4 hours to bind the retrovirus vector.

Each well was washed twice with 500 µl of PBS (phosphate-buffered saline), 0.1% bovine serum albumin (BSA, Fraction V, Sigma) in PBS, 1% bovine serum albumin in PBS, X-VIVO 15 (Cambrex), X-VIVO 10 (Cambrex), IMDM (Invitrogen) or RPMI1640 (Sigma). The well was filled with 500 µl of the same solution, and the plate was incubated at 4° C. for 7 days. In addition, the virus supernatant was added to each well, and the plate was incubated for 7 days without washing (the virus supernatant was incubated as it was). On day 7, the solution was removed, 500 µl of a suspension containing K-562 cells at a density of $4\times10^4$ cells/ml was added, and the cells were cultured in the presence of 5% $CO_2$ at 37° C. for gene transfer. As a control, a virus-bound plate was prepared using a virus supernatant of the same lot and the same procedure, and K-562 cells were added immediately without incubation at 4° C. for gene transfer. Gene transfer efficiency was determined for the cells using expression of rsGFP gene as an index. Values of gene transfer efficiency with the virus relative to transfer efficiency observed for the control after incubation for 7 days are shown in FIG. 1.

As shown in FIG. 1, higher activities were retained using all the solutions as compared with that observed for the virus supernatant that was allowed to stand as it was. Thus, it was shown that storage of a retrovirus being separated from a supernatant of a retrovirus producer cell was effective. In particular, a solution containing bovine serum albumin proved to be effective in stable storage.

Example 3

Storage of Retrovirus Using CH-296-Coated Plate (2)

It was shown in Example 2 that storage stability was increased by washing a retrovirus-bound container. Next, influence of the following substances on storage of a retrovirus was examined in order to search for a solution that can contribute more to increase in storage stability: inorganic salts (sodium phosphate; a mixture of calcium chloride and magnesium sulfate; a mixture of sodium phosphate, calcium chloride and magnesium sulfate); saccharides (glucose; D-sorbitol; refined white sugar; maltose; fructose; lactose; D-mannitol); macromolecular compounds (carmellose sodium; methylcellulose; hydroxypropyl cellulose; propylene glycol; polyethylene glycol 400); proteins (purified gelatin; human serum albumin (HSA)). Among the above-mentioned substances, inorganic salts were dissolved in water for injection and other substances were dissolved in PBS. Then, their effects on retrovirus storage stability were tested. The procedure for the search followed that of Example 2 except that the storage incubation of a retrovirus-bound container was carried out at 37° C. for 3 hours. As a result, increase in retrovirus vector storage stability was observed using the following as compared with PBS alone: 40 mM sodium phosphate buffer (pH 7); 0.5 mM calcium chloride and 1 mM magnesium sulfate in 20 mM phosphate buffer (pH 7); 1.5-20% human serum albumin in PBS; 0.5-2.5% purified gelatin in PBS; or 5% lactose in PBS.

Figure 2:
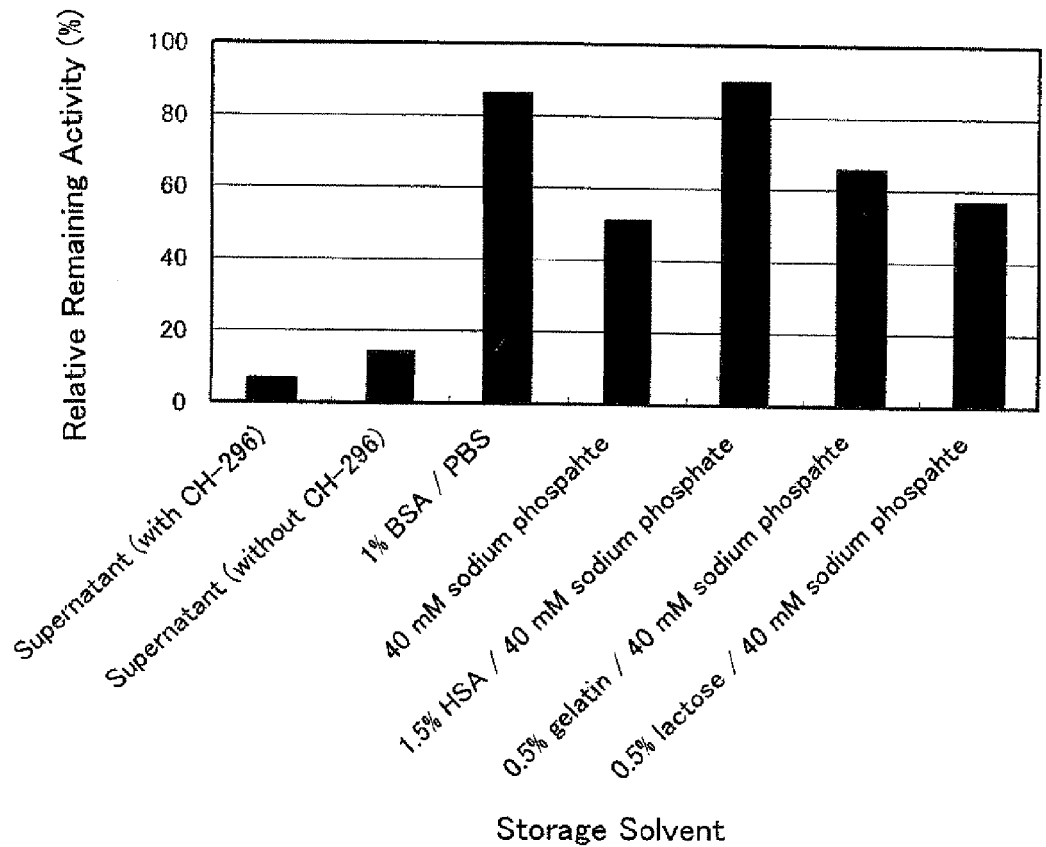
FIG. 2 shows values of gene transfer efficiency relative to transfer efficiency observed for the control.

As a result of the above-mentioned tests, it was shown that there was a tendency that 40 mM sodium phosphate buffer was superior to PBS as a basal solvent, and proteins and saccharides increased the stability. Then, retrovirus storage stability tests were carried out at 4° C. for 7 days according to the procedure as described in Example 2 using the following: 1% bovine serum albumin in PBS; 1.5% human serum albumin in 40 mM sodium phosphate buffer; 0.5% purified gelatin in 40 mM sodium phosphate buffer; or 5% lactose in 40 mM sodium phosphate buffer. pH of the sodium phosphate buffer was 7.0 in all cases. Values of gene transfer efficiency with the virus relative to transfer efficiency observed for the control after incubation for 7 days were calculated and are shown in FIG. 2. As shown in the figure, it was shown that the storage stability was dramatically increased by storage after exchange for the respective solutions as compared with the storage of the retrovirus producer cell supernatant as it was.

Example 4

Storage of Retrovirus in the Presence of Various Functional Substances

In this Example, storage stability was assessed using a functional substance that exhibits a retrovirus-binding activity and a cell adhesion activity. Besides CH-296, the following was used as a functional substance that exhibits a retrovirus-binding activity and a cell adhesion activity: CH-271 or H-296 (Kimizuka, F. et al., J. Biochem., 110(2):284-291 (1991)); DEAE-dextran (Sigma); poly-L-lysine (average molecular weight of 30,000 to 70,000, ICN); a mixture of DEAE-dextran and a fibronectin fragment C-CS1 (Kimizuka, F. et al., J. Biochem., 110(2):284-291 (1991)); or a mixture of poly-L-lysine and C-CS1.

500 µl of a fibronectin fragment CH-296, CH-271 or H-296 (20 µg/ml), DEAE-dextran in PBS (0.9 mg/ml), or poly-L-lysine in PBS (40 µg/ml) was added to each well of a 24-well plate without surface treatment (Falcon). The mixture of DEAE-dextran and C-CS1 and the mixture of poly-L-lysine and C-CS1 were prepared by adding C-CS1 to the DEAE-dextran solution or the poly-L-lysine solution at a final concentration of 4.4 µg/ml. The plate was allowed to stand at 4° C. overnight, subjected to blocking with 2% BSA/PBS at room temperature for 30 minutes, and washed with PBS. This plate was used as a functional substance-coated plate and subjected to retrovirus storage stability tests.

Retrovirus storage stability tests were carried out using the plate coated with the respective functional substances according to the procedure as described in Example 2. The tests were carried out in the following three virus storage manners: storage of the virus supernatant as it was; storage in 40 mM sodium phosphate buffer (pH 7.0); and storage in 1.5% human serum albumin in 40 mM sodium phosphate buffer (pH 7.0). Values of gene transfer efficiency with the virus relative to transfer efficiency observed for the control after incubation for 7 days were calculated and are shown in Table 1.

Gene transfer efficiency was retained at a high level not only using a plate coated with the polypeptide having the heparin-II domain of fibronectin (CH-296, CH-271 or H-296) but also using a plate coated with DEAE-dextran or polylysine. It was shown that storage of a retrovirus using such a substance was effective. In addition, the coexistence of the substance having a cell-binding activity (C-CS1) did not influence the storage with the above-mentioned substance.

TABLE 1

|  | Virus supernatant | 40 mM sodium phosphate buffer | 1.5% human serum albumin in 40 mM sodium phosphate buffer |
| --- | --- | --- | --- |
| CH-296 | 9.27 | 54.69 | 88.58 |
| CH-271 | 12.30 | 54.57 | 88.65 |
| H-296 | 9.91 | 47.51 | 83.36 |
| DEAE-dextran | 10.96 | 81.63 | 106.49 |

TABLE 1-continued

|  | Virus supernatant | 40 mM sodium phosphate buffer | 1.5% human serum albumin in 40 mM sodium phosphate buffer |
|---|---|---|---|
| DEAE-dextran + C-CS1 | 12.77 | 59.18 | 101.87 |
| Polylysine | 8.54 | 48.45 | 80.77 |
| Polylysine + C-CS1 | 8.42 | 52.60 | 81.31 |

(Values in % are shown in the table.)

Example 5

Storage of Retrovirus Using Gas-Permeable Culture Bag

CH-296 was used for a 24-well plate without surface treatment (Falcon) or a gas-permeable culture bag (X-FOLD™, 85 cm², Nexell), and the following experiments were carried out.

X-FOLD™ was coated with CH-296 as follows.

First, 9 ml of CH-296 (20 µg/ml) was added to each bag and the bag was allowed to stand at 4° C. overnight. The bag was then washed three times with 30 ml of PBS to obtain a CH-296-coated bag. A 24-well plate was coated with CH-296 according to the procedure as described in Example 1.

500 µl of a 4-fold dilution of the GaLV/DOG-polII virus supernatant was added to each well of a 24-well CH-296-coated plate, and the plate was incubated in 5% $CO_2$ incubator at 37° C. for 4 hours to bind the retrovirus vector. 22 ml of the same GaLV/polII virus supernatant dilution was added to X-FOLD™, air was removed from the bag, and the bag was sealed and incubated in the presence of 5% $CO_2$ at 37° C. for 4 hours to bind the retrovirus vector. The containers were washed twice with 40 mM sodium phosphate buffer (pH 7.0) or 1.5% human serum albumin in 40 mM sodium phosphate buffer (pH 7.0) (500 µl for the 24-well plate, 30 ml for the bag). The well or the bag was filled with the same solution; in case of the bag, the bag was sealed after removing air; and the plate or the bag was incubated at 4° C. for 7 days. In addition, the same virus supernatant dilution was added to the CH-296-coated plate or the CH-296-coated bag; in case of the bag, the bag was sealed after removing air; and the plate or the bag was incubated at 4° C. for 7 days as it was. On day 7, the solution was removed from the container, a suspension containing K-562 cells at a density of 4×10⁴ cells/ml (500 µl for the 24-well plate, 22 ml for the bag) was added, and the plate or the bag was incubated in the presence of 5% $CO_2$ at 37° C. for gene transfer. As a control, a virus-bound container was prepared using a virus supernatant of the same lot and the same procedure, and K-562 cells were added immediately without incubation at 4° C. for gene transfer. Values of gene transfer efficiency relative to gene transfer efficiency observed for the control after incubation for 7 days were calculated.

Gene transfer efficiency of only 10% or less as compared with the control was observed when the retrovirus supernatant dilution was stored in the plate as it was. On the other hand, gene transfer efficiency of more than 60% as compared with the control was observed when storage was carried out in the sealed bag or when the solution was exchanged by washing the container after binding the retrovirus to CH-296 (the plate or the bag). Based on these results, it was shown that when a retrovirus was stored in the presence of a substance having a retrovirus-binding activity, decrease in infectivity of the retrovirus was dramatically suppressed by preventing the retrovirus-containing solution from contacting air and/or separating the retrovirus from the retrovirus producer cell supernatant.

Example 6

Long-Term Storage of Retrovirus

A GaLV/DOG-polII virus supernatant (3.3×10⁵ I.V.P./ml) was diluted with RPMI-1640 medium containing 10% fetal calf serum to prepare a 2-fold dilution. 500 µl of the dilution was added to each well of a 24-well CH-296-coated plate prepared as described in Example 1, and the plate was incubated in 5% $CO_2$ incubator at 37° C. for 4 hours to bind the retrovirus vector. Each well of the plate was washed twice with 500 µl of 40 mM sodium phosphate buffer (pH 7.0) or 1.5% human serum albumin in 40 mM sodium phosphate buffer (pH 7.0). The well was filled with the same buffer, and the plate was incubated at 4° C. In addition, the 2-fold dilution of the virus supernatant was added to each well, and the plate was incubated at 4° C. without washing (the virus supernatant was incubated as it was). The solution was removed from the well 1, 2, 3 or 4 week(s) after the initiation of incubation, 500 µl of a suspension containing K-562 cells at a density of 4×10⁴ cells/ml was added, and the cells were cultured in the presence of 5% $CO_2$ at 37° C. for gene transfer. As to the well incubated with the virus supernatant as it was, the well was washed once with 500 µl of 40 mM sodium phosphate buffer (pH 7.0), and 500 µl of a suspension containing K-562 cells at a density of 4×10⁴ cells/ml was added, and the cells were cultured in the presence of 5% $CO_2$ at 37° C. for gene transfer. As a control, a virus-bound plate was prepared using a virus supernatant of the same lot and the same procedure, and K-562 cells were added immediately without incubation at 4° C. for gene transfer. Gene transfer efficiency was determined for the cells subjected to gene transfer. Values of gene transfer efficiency with the virus relative to transfer efficiency observed for the control (i.e., remaining titers) were calculated for the respective test groups and are shown in Table 2.

TABLE 2

|  | After 1 week | After 2 weeks | After 3 weeks | After 4 weeks |
|---|---|---|---|---|
| 40 mM phosphate buffer | 80.46 | 63.44 | 47.55 | 40.76 |
| Human serum albumin in 40 mM phosphate buffer | 96.19 | 88.75 | 73.23 | 58.93 |
| Virus supernatant | 56.89 | 6.24 | 2.87 | 1.98 |

(Values in % are shown in the table.)

As shown in Table 2, when the virus supernatant was stored as it was, the titer was reduced by one tenth or below after 2 weeks. On the other hand, when the retrovirus was separated from the culture supernatant (the culture supernatant was replaced by another buffer), 40% or more of the titer was retained after storage for 4 weeks. Particularly fine storage stability was observed when a buffer containing a protein (human serum albumin) was used.

Example 7

Storage of Diluted Retrovirus

A GaLV/DOG-polII virus supernatant (3.3×10⁵ I.V.P./ml) was diluted with RPMI-1640 medium containing 10% fetal calf serum to prepare 2-, 4-, 8- or 16-fold dilutions. 500 µl of the dilution was added to each well of a 24-well CH-296- coated plate prepared as described in Example 1, and the plate was incubated in 5% $CO_2$ incubator at 37° C. for 4 hours to bind the retrovirus vector. Each well of the plate was washed twice with 500 µl of 40 mM sodium phosphate buffer (pH 7.0) or 1.5% human serum albumin in 40 mM sodium phosphate buffer (pH 7.0). The well was filled with 500 µl of the same buffer, and the plate was incubated at 4° C. In addition, one of the virus supernatant dilutions was added to each well, and the plate was incubated at 4° C. without washing (the virus supernatant was incubated as it was). The solution was removed from the well 1, 2, 3 or 4 week(s) after the initiation of incubation, 500 µl of a suspension containing K-562 cells at a density of $4\times10^4$ cells/ml was added, and the cells were cultured in the presence of 5% $CO_2$ at 37° C. for gene transfer. As to the well incubated with the virus supernatant as it was, the well was washed once with 500 µl of 40 mM sodium phosphate buffer (pH 7.0), and 500 µl of a suspension containing K-562 cells at a density of $4\times10^4$ cells/ml was added, and the cells were cultured in the presence of 5% $CO_2$ at 37° C. for gene transfer. As a control, a virus-bound plate was prepared using a virus supernatant of the same lot and the same procedure, and K-562 cells were added immediately without incubation at 4° C. for gene transfer. Gene transfer efficiency was determined for the cells subjected to gene transfer. Values of gene transfer efficiency with the virus relative to transfer efficiency observed for the control after storage (i.e., remaining titers) were calculated and are shown in Table 3.

TABLE 3

|  | After 1 week | After 2 weeks |
|---|---|---|
| 40 mM phosphate buffer | | |
| 2-fold dilution | 71.91 | 64.56 |
| 4-fold dilution | 64.48 | 50.69 |
| 8-fold dilution | 59.06 | 43.90 |
| 16-fold dilution | 58.94 | 44.28 |
| Human serum albumin in 40 mM phosphate buffer | | |
| 2-fold dilution | 96.24 | 90.12 |
| 4-fold dilution | 94.56 | 85.16 |
| 8-fold dilution | 91.76 | 86.87 |
| 16-fold dilution | 101.96 | 99.02 |
| Virus supernatant | | |
| 2-fold dilution | 48.30 | 8.34 |
| 4-fold dilution | 38.80 | 7.35 |
| 8-fold dilution | 29.80 | 6.65 |
| 16-fold dilution | 28.24 | 7.64 |

(Values in % are shown in the table.)

As shown in Table 3, when the virus supernatant dilution was stored as it was, rapid decrease in titer was observed regardless of the dilution rate. On the other hand, when the virus supernatant dilution was subjected to binding to the plate and the culture supernatant was then replaced by another buffer, the decrease in titer was remarkably suppressed. The dilution rate of the virus supernatant used did not considerably influence the storage stability of the virus titer. Particularly, when a buffer containing a protein (human serum albumin) was used, influence by the dilution rate was not observed at all. Based on these results, it was shown that the method of the present invention was effective in storage of a retrovirus in a low-titer or diluted virus supernatant.

INDUSTRIAL APPLICABILITY

The present invention provides a method for storing a retrovirus and a composition containing a retrovirus. According to the storage method, a retrovirus can be stored in a state ready for immediate use for infection of a cell. Thus, it is useful for studies of retroviruses and in the field of medicine including gene therapy. The composition is also useful in the same field.

The invention claimed is:
1. A method for stably storing a retrovirus, comprising:
   (1) contacting a solid support on which a substance having a retrovirus-binding activity is immobilized with a retrovirus producer cell culture supernatant which contains the retrovirus;
   (2) removing the retrovirus producer cell culture supernatant in step (1) from contact with the solid support;
   (3) after removal of the retrovirus producer cell culture supernatant, contacting the solid support on which the retrovirus is bound via the substance having a retrovirus-binding activity immobilized on the solid support with a solution containing at least one substance selected from the group consisting of gelatin, albumin and lactose; and
   (4) storing the retrovirus, bound to the solid support via the substance having a retrovirus-binding activity immobilized on the solid support obtained in step (3), in contact with the solution and in an unfrozen state for a period of 24 hours or more.
2. The method according to claim 1, wherein the retrovirus is stored in contact with the solution so that the solution is not in contact with air.
3. The method according to claim 1, wherein the solution contains a phosphate salt as a buffering component.
4. The method according to claim 1, wherein one substance of the at least one substance contained in the solution is bovine serum albumin (BSA) or human serum albumin (HSA).
5. The method according to claim 1, wherein the period of storage is 48 hours or more.
6. The method according to claim 5, wherein the period of storage is 72 hours or more.
7. The method according to claim 1, wherein the storing step is carried out at a temperature of 15° C. or below.
8. The method according to claim 7, wherein the storing step is carried out at a temperature of 0-10° C.
9. The method according to claim 1, wherein the solid support is a container selected from the group consisting of a culture plate, a culture flask, a separation bag, and a gas-permeable culture bag.

* * * * *